(12) United States Patent
McAnalley et al.

(10) Patent No.: US 7,999,003 B2
(45) Date of Patent: Aug. 16, 2011

(54) ANTIOXIDANT COMPOSITIONS AND METHODS THERETO

(75) Inventors: Bill H. McAnalley, Grand Prairie, TX (US); Eileen Vennum, Grand Prairie, TX (US); Shayne A. McAnalley, Galveston, TX (US); C. Michael Koepke, Grand Prairie, TX (US)

(73) Assignee: Mannatech, Incorporated, Coppell, TX (US)

( * ) Notice: Subject to any disclaimer, the term of this patent is extended or adjusted under 35 U.S.C. 154(b) by 1158 days.

(21) Appl. No.: 10/648,047

(22) Filed: Aug. 26, 2003

(65) Prior Publication Data
US 2005/0048143 A1 Mar. 3, 2005

(51) Int. Cl.
*A61K 35/78* (2006.01)
*A61K 31/7048* (2006.01)

(52) U.S. Cl. .......... 514/456; 424/729; 424/766; 514/27; 514/904; 514/458; 422/68.1

(58) Field of Classification Search ............ 422/68; 424/729, 766; 514/27, 456, 458, 904
See application file for complete search history.

(56) References Cited

U.S. PATENT DOCUMENTS

| | | | |
|---|---|---|---|
| 5,427,951 A | 6/1995 | Davies et al. | |
| 6,063,403 A | 5/2000 | de Haan et al. | |
| 6,086,910 A | 7/2000 | Howard et al. | |
| 6,114,177 A | 9/2000 | Naguib | |
| 6,177,260 B1 | 1/2001 | Benzie et al. | |
| 6,231,877 B1 | 5/2001 | Vacher et al. | |
| 6,291,533 B1 * | 9/2001 | Fleischner | 514/682 |
| 6,365,622 B1 | 4/2002 | Cavazza | |
| 6,429,021 B1 | 8/2002 | Qian et al. | |
| 6,562,869 B1 | 5/2003 | Hamilton et al. | |
| 6,607,919 B1 | 8/2003 | Popv et al. | |
| 6,642,277 B1 * | 11/2003 | Howard et al. | 514/783 |
| 6,805,880 B1 | 10/2004 | Højgaard et al. | |
| 2002/0182736 A1 | 12/2002 | Aldini et al. | |
| 2002/0192314 A1 * | 12/2002 | Cho et al. | 424/766 |

OTHER PUBLICATIONS

Brand, Jennie C. et al., An Outstanding Food Source of Vitamin C, 1982, The Lancet, vol. 320 Issue 8303, p. 873.*
AlSheikhly et al., "Chain-Propagation Length of Linoleic Acid Peroxidation in Aqueous Monomeric and Micellar Systems", J. Phys. Chem. (1989), vol. 93, pp. 3103-3106.
Barclay et al., "Benzophenone-photosensitized autoxidation of linoleate in solution and sodium dodecyl sulfate micelles", Can. J. Chem. (1987), vol. 65, p. 2529-2540.

(Continued)

*Primary Examiner* — Krishnan S Menon
*Assistant Examiner* — Rebecca Fritchman
(74) *Attorney, Agent, or Firm* — Edwin S. Flores; Daniel J. Chalker; Chalker Flores, LLP

(57) ABSTRACT

The present invention provides a performance assay that measures the total antioxidant activity of a composition using oxygen uptake in contrast to prior art methods that measure antioxidant capacity by indirectly measuring degradation of a fluorescent compound by following the disappearance of fluorescence. Using the performance antioxidant assay of the present invention, an antioxidant composition having synergistic activity is provided by the present inventors that includes flavonoids such as the flavonol quercetin, mixed tocopherols or tocotrienols, grape skin extract, green tea extract and bush plum. The antioxidant activity of the present composition exceeds 6,000 micromoles Trolox equivalent units per gram using the present invention.

16 Claims, 5 Drawing Sheets

OTHER PUBLICATIONS

Burton et al., "Autoxidation of Biological Molecules. 1. The Antioxidant Activity of Vitamin E and Related Chain-Breaking Phenolic Antioxidants in Vitro", J. Am. Chem. Soc. (1981), vol. 103, pp. 6472-6477.

Cao et al., "Increases in human plasma antioxidant capacity after consumption of controlled diets high in fruit and vegetables," Am. J. Clin. Nutr. (1998), vol. 68, pp. 1081-1087.

Castle et al., "Inhibition Kinetics of Chain-Breaking Phenolic Antioxidants in SDS Micelles. Evidence That Intermicellar Diffusion Rates May Be Rate-Limiting for Hydrophobic Inhibitors Such as $\alpha$-Tocopherol", J. Am. Chem. Soc. (1986), vol. 108, pp. 6381-6382.

Cosgrove et al. "The Kinetics of the Autoxidation of Polyunsaturated Fatty Acids", Lipids (1987), vol. 22, pp. 299-304.

Halliwell et al., "Free Radicals in Biology and Medicine," Oxford University Press, 2001, pp. 55-72.

Huang et al., "Development and Validation of Oxygen Radical Absorbance Capacity Assay for Lipophilic Antioxidants Using Randomly Methylated $\beta$-Cyclodextrin as the Solubility Enhancer," J. Agric. Food Chem. (2002), vol. 50, pp. 1815-1821.

Niki et al., "Inhibition of Oxidation of Methyl Linoleate in Solution by Vitamin E and Vitamin C", J. Biol. Chem. (1984), vol. 259, pp. 4177-4182.

Ou et al., "Development and Validation of an Improved Oxygen Radical Absorbance Capacity Assay Using Fluorescein as the Fluorescent Probe," J. Agric. Food Chem. (2001), vol. 49, pp. 4619-4626.

Packer et al., "Direct observation of a free radical interaction between vitamin E and vitamin C," Nature (1979), vol. 278, pp. 737-738.

Pryor et al., "A Rapid Screening Test to Determine the Antioxidant Potencies of Natural and Synthetic Antioxidants", J. Org. Chem. (1993), vol. 58, pp. 3521-3532.

Pryor et al., Comparison of the Efficiencies of Several Natural and Synthetic Antioxidants in Aqueous Sodium Dodecyl Sulfate Micelle Solutions, J. Am. Chem. Soc. (1988), vol. 110, pp. 2224-2229.

Pryor et al., "Autoxidation of Micelle-Solubilized Linoleic Acid. Relative Inhibitory Efficiencies of Ascorbate and Ascorbyl Palmitate", J. Org. Chem., (1985), vol. 50, pp. 281-283.

Yilmaz et al., "Reaction of $\beta$-carotene and AAPH in phosphate buffer during the oxygen radical absorbance capacity (ORAC) assay," Food Science and Technology (2001).

International Search Report issued Mar. 29, 2005, in connection with International Application No. PCT/US2004/027644.

Written Opinion of the International Searching Authority issued Mar. 29, 2005, in connection with International Application No. PCT/US2004/027644.

International Preliminary Report on Patentability issued Aug. 15, 2005 in connection with International Application No. PCT/US2004/027644.

International Search Report issued Sep. 12, 2005, in connection with International Application No. PCT/US05/06924.

Written Opinion of the International Searching Authority issued Sep. 12, 2005, in connection with International Application No. PCT/US05/06924.

* cited by examiner

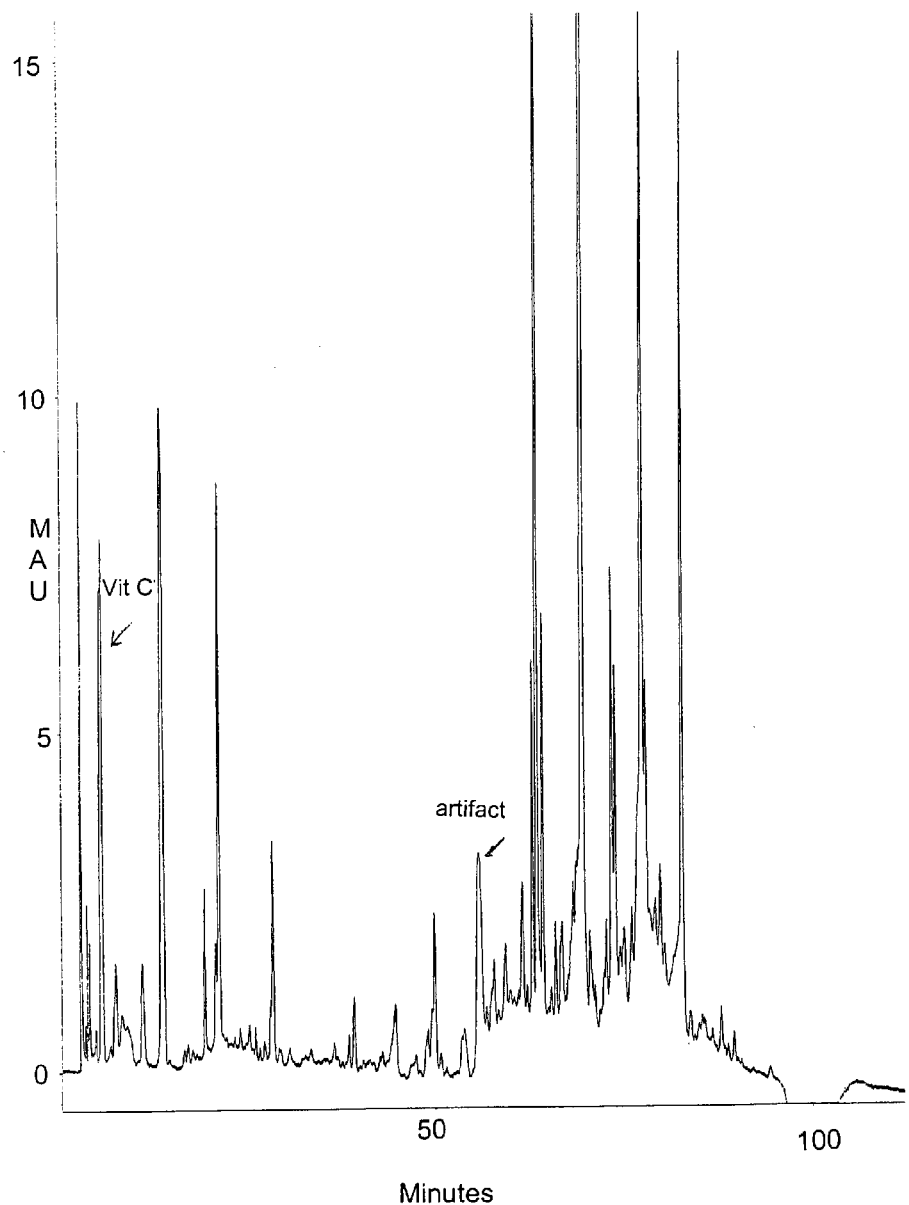

ANTIOXIDANT COMPOSITIONS AND METHODS THERETO

FIELD OF THE INVENTION

The present invention relates to the field of measuring antioxidant activity of a composition including both lipophilic and hydrophilic antioxidants in a single assay. The present invention also relates to antioxidant compositions having a synergistic antioxidant activity, the compositions comprising water soluble and lipid soluble ingredients. Further, a method of screening antioxidant preparations for antioxidant capacity is provided.

BACKGROUND OF THE INVENTION

Biological systems have developed antioxidant systems to combat the effects of radicals and other pro-oxidative species. An antioxidant is any substance that significantly delays or prevents oxidation of an oxidizable substrate. Certain enzymes are antioxidants such as superoxide dismutase and catalase, which are coded for by many organisms. Substances such as vitamin C and plant phenols are antioxidants introduced through the diet into biological systems. It has been proposed that naturally occurring levels of these substances are not adequately produced in the body or ingested in the normal diet. The normal diet often does not provide enough antioxidants because it is deficient in fruits and vegetables. Further, fruits and vegetables that are in the diet are likely depleted of their antioxidants due to modem-day processing. The normal diet could be improved, but taking into account today's lifestyles and poor composition of Western foods many choose to supplement their normal diet with antioxidants.

While a tremendous amount of research has gone into use of antioxidants as nutritional supplements, supplementation of the modem diet has not been consistently successful (European Research on Functional Effects of Dietary Antioxidants, Sept. 25-28, 2002, Cambridge, UK). Problems with accurately and consistently measuring antioxidant capacity under various conditions and of measuring compositions having varying amounts of lipophilic versus hydrophilic ingredients have not been solved.

Several laboratory methods have been developed to determine the ability of a substance to quench a free radical or to determine its antioxidant capacity. For a review, see Halliwell B., and Gutteridge J. M. C., *Free Radicals in Biology and Medicine*. 3rd Edition. New York: Oxford University Press, 2000. These assays are the TEAC, $^{19}$F-NMR, TRAP, modified TRAP, FRAP, the Glazer fluorescence-based method, the phosphomolybdenum complex method, and the ORAC, all of which are proposed to measure some aspect of a substance's ability to quench free radical species.

Prior ORAC assays for antioxidant capacity rely on the generation of a radical that oxidizes a substrate. In the presence of an antioxidant, the oxidation of the substrate is slowed. The protective effect of an antioxidant is measured by determining the area under a decay curve (AUC) of the test sample as compared to a blank. A method called oxygen radical absorbance capacity (ORAC (β-PE)) measures antioxidant activity against peroxyl radical induced by 2,2'-azo-bis(2-amidinopropane) dihydrochloride (AAPH) at 37° C. β-phycoerythrin (β-PE) was used in these assays as a fluorescent probe where loss of fluorescence of β-PE is an indication of the extent of damage from its reaction with a peroxyl radical.

Several drawbacks of using β-PE as a probe led Ou et al. (*J Agric Food Chem.* 2001;49(10):4619-4626) to develop an assay using fluorescein as the fluorescent probe (ORAC (fl)). However, the fluorescein system does not measure antioxidant capacity of lipophilic samples since the assay is performed in aqueous solution. A modification of the ORAC (fl) method was described by Huang et al. (*J Agric Food Chem.* 2002;50(7):1815-1821) for lipophilic antioxidants using randomly methylated beta-cyclodextrin as a solubility enhancer. The reaction mechanism was determined to be that of hydrogen atom transfer. The ORAC (fl) method using beta-cyclodextrin does not measure antioxidant activity of carotenoids and polyunsaturated fatty acids since carotenoids and fatty acids are not chain-breaking antioxidants (Huang et al. ibid). These antioxidants may act as singlet oxygen scavengers and may follow a different reaction mechanism. The ORAC (fl) method has been accepted by the industry as the gold standard for measuring antioxidant capacity.

U.S. published patent application 2002/0182736 to Aldini et al. describes a method that is alleged to determine the total antioxidant activity of a sample in both lipid and aqueous compartments. The sample is incubated with a lipophilic radical generator and an oxidizable lipophilic indicator in a lipid compartment of the sample. Oxidation of the oxidizable lipophilic indicator provides a measure of the antioxidant activity of the lipid compartment of the sample. The sample is also incubated with a hydrophilic radical generator and an oxidizable hydrophilic indicator in an aqueous compartment of the sample. Oxidation of the oxidizable hydrophilic indicator provides a measure of the antioxidant activity of the aqueous compartment of the sample. HPLC and fluorescence assays were used to determine these separate values.

The present inventors observed that assays using the ORAC (fl) provided data that showed an increase in fluorescence after addition of the radical initiator. The ORAC (fl) relies on the assumption that fluorescein is the only fluorescent component being measured. In fact, any molecule having absorbance, fluorescence or phosphorescence at the wavelength measured in the ORAC (fl) contributes to the values obtained from this assay. Further, such measured absorbance, fluorescence, or phosphorescence may not be related to antioxidant capacity as demonstrated by initial rise in fluorescence values. Therefore, any compound in a complex sample that fluoresces at the same wavelength as fluorescein will also be measured causing a skewed result.

Oxygen uptake has been previously used as a measure of antioxidant activity. The discovery that aqueous dispersions of oxidizable organic compounds can be readily and reproducibly initiated at a constant rate, $R_i$, by peroxidation using the water-soluble azo compound 2,2'-azo-bis-(2-amidipropane hydrochloride), ABAP, is the basis of the Total Radical-Trapping Antioxidant Parameter, TRAP, method developed by Wayner et al. (*FEBS Lett.* 1985;187(1):33-37). Upon addition of the ABAP to plasma, the length of time that oxygen uptake by peroxidizable plasma is inhibited is measured with an oxygen probe, and this value is referred to as the TRAP. Trolox (a synthetic antioxidant used as a standard) is used in this method to induce a second reaction period after the natural antioxidants have been depleted. This second induction period is used to calculate an $R_i$ value, which is used to calculate the TRAP value. The TRAP value is reported as the number of moles of peroxyl radicals trapped per liter of fluid.

The duration of time is the only parameter measured in the TRAP method and is a limiting factor in its analysis. The time taken to prevent maximum oxygen uptake cannot be measured easily and precisely, and the total radical trapping capability per mole of some antioxidants is dependent on their initial concentration. This analysis leaves out the extent of inhibition.

A modified TRAP assay was later published by Ghiselli et al. (*Free Radic. Biol. Med.* 1995;18(1):29-36), which corrects for interferences from plasma proteins or sample dilution. This modified method is based on the ability of plasma to protect β-PE from peroxyl radical attack produced by ABAP. Protection is accomplished by precipitating the protein out of plasma with ammonium sulfate and ultracentrifugation. The modified TRAP assay is performed by adding the reagents to quartz fluorometer cells and, after a 37° C. incubation for 5 minutes, ABAP is added. Fluorescence is monitored at 495 nm every 5 minutes maintaining the same temperature throughout the experiment.

This modified TRAP method produces a linear decrease in fluorescence due to the thermal decomposition of ABAP. A period of total protection is indicated by a lag phase upon the addition of any antioxidant compound. It is assumed that the total plasma antioxidant capacity is directly related to the length of the lag phase. The TRAP is quantified by comparing the lag phase produced by the antioxidant compound to the lag phase produced by a Trolox solution of known concentration. The modified TRAP method does not measure the ability of plasma to break the lipid peroxidation chain triggered by ABAP, and it is not fully defined whether and to what extent lipid-soluble antioxidants are involved in TRAP.

The present invention addresses these problems in the art and provides an assay that measures oxygen uptake of a complete system, allowing for selection of optimum ratios of ingredients for an antioxidant composition. An optimized synergistic antioxidant composition is also provided.

SUMMARY OF THE INVENTION

The present invention is based, in part, on a new method of measuring antioxidant activity of a composition by measuring oxygen uptake of a system and by dissolving a test composition in a detergent-containing solvent at less than saturation conditions.

Further, the present invention provides an antioxidant composition having synergistic antioxidant activity that, while not wanting to be bound by theory, is believed by the present inventors to have activity for protecting intracellular cytosol, cellular membranes, and extracellular fluid such that the body is protected throughout by antioxidant activity.

An effective antioxidant supplement prevents the buildup of unpaired electrons in an organelle or body fluid. Different antioxidants concentrate in different areas of a cell or organelle, depending on whether the antioxidants are lipid- or water-soluble or synthesized in a specific cellular compartment (e.g. glutathione in the cytosol). If more of a particular category of antioxidants (i.e., fat-soluble, water-soluble) is available in a particular organelle or body fluid than is needed to balance the available unpaired electrons, that antioxidant concentrates in and serves as a "sink" for unpaired electrons, producing superoxide radicals, peroxide radicals, or hydroxyl radicals at a faster rate, i.e. it actually becomes a pro-oxidant. For this antioxidant-mediated process the present inventors coined the term "antioxidant capacitor effect."

For example, vitamin E, a lipid-soluble vitamin, concentrates in the lipid membranes of cells. If more of this vitamin is available than is needed to balance the unpaired electrons in the membrane, and/or there is an insufficient amount of co-antioxidants available to regenerate the vitamin E, tocopherol-mediated peroxidation is believed to occur. That is, vitamin E is believed to concentrate in the lipid membranes and serves as a "sink" for unpaired electrons producing peroxide radicals in the membrane at a faster rate. Thus, when taken in excessive, disproportional amounts, vitamin E actually becomes a pro-oxidant. This is the antioxidant capacitor effect. A similar effect can result whenever an imbalance occurs (whether in fat-soluble or water-soluble areas) that impedes elimination of free radicals from the body.

The present invention provides an antioxidant composition comprising a flavonoid selected from the group consisting of a flavone, a flavonol, an isoflavone, an isoflavonol, an analogue thereof, a pharmaceutically acceptable salt thereof, and a mixture thereof; and a mixture of at least two forms of vitamin E selected from the group consisting of alpha, beta, delta, epsilon, gamma, zeta, eta, xi1, xi2, and sigma tocopherols, and alpha, beta, delta and gamma tocotrienols, and derivatives thereof; wherein the ratio of flavonoid to mixture of vitamin E forms is 40/60 to 90/10 precent by weight. The antioxidant composition may further comprise bush plum, green tea extract, grape skin extract, or a mixture thereof.

The flavonoid and mixture of vitamin E forms are defined herein as "primary ingredients," and the primary ingredients are present in the antioxidant compositions of the present invention in an amount of 12.1% up to 100% by weight, of 30% to 85% by weight, or, in another embodiment, 82% by weight.

The bush plum, green tea extract, grape skin extract, or a mixture thereof are defined herein as "secondary ingredients," and the secondary ingredients are present in the antioxidant compositions of the present invention in an amount of greater than 0% to 87.9% by weight, of 15% to 70% by weight, or, in another embodiment, 18% by weight. In another embodiment, the secondary ingredients include a combination of grape skin extract and green tea extract present in the composition in a weight ratio of 60/40 to 80/20. In a further embodiment, the antioxidant composition further comprises bush plum in an amount of 2% by weight of the composition.

In one embodiment of the antioxidant composition, the flavonoid is a flavonol, and the flavonol is selected from the group consisting of quercetin, kaempferol, myricetin, an analogue thereof, a pharmaceutically acceptable salt thereof, and a mixture thereof. In a further embodiment of the invention, the flavonol is quercetin.

In another embodiment of the invention, the vitamin E forms are selected from the group consisting of alpha, beta, delta, and gamma tocopherol.

An embodiment of the invention is an antioxidant composition comprising quercetin, a mixture of alpha, beta, delta, and gamma tocopherols, grape skin extract, green tea extract, and bush plum wherein the quercetin and mixture of alpha, beta, delta, and gamma tocopherols comprise 12.1% up to 100% by weight of the composition, and wherein the quercetin and mixture of alpha, beta, delta, and gamma tocopherols are present in a weight percent ratio of 40/60 to 90/10. In one embodiment of the invention, the quercetin, tocopherols, grape skin extract, green tea extract, and bush plum have weight ratios of 49/33/9.5/6.5/2. In such an embodiment, the antioxidant activity is at least 10,000 micromoles Trolox equivalent units per gram, using an ORAC(o) oxygen uptake measuring assay.

According to a further embodiment, the antioxidant composition of the present invention further comprises a carrier comprising gum acacia, xanthan gum, gum tragacanth, gum ghatti, and aloe vera gel extract, wherein the composition and carrier have a weight ratio of 1:2 to 2:1. The carrier components, namely, gum acacia, xanthan gum, gum tragacanth, gum ghatti, and aloe vera gel extract are present in the carrier in a weight ratio of 30/30/20/19/1. The antioxidant composition and carrier combination may be roller-compacted and, according to one embodiment, is roller compacted at a weight ratio of 1:2.

A method for measuring antioxidant activity of a test sample having water and lipid-soluble ingredients by measuring oxygen uptake is a further embodiment of the present invention. The method comprises combining an oxidizable target molecule and the test sample in a solvent of acetone/water/detergent to form a test mixture at 37° C. under conditions where oxygen is present in equilibrium with air; adding an azo radical initiator to the test mixture; and measuring area under an oxygen uptake curve of the test mixture to provide a measure of the antioxidant activity of the test sample. This method may further comprise the steps of combining an oxidizable target molecule and a solvent of acetone/water/detergent to form a control mixture at 37° C. under conditions where oxygen is present in equilibrium with air; combining an oxidizable target molecule and Trolox in a solvent of acetone/water/detergent to form a standard mixture at 37° C. under conditions where oxygen is present in equilibrium with air; adding an azo radical initiator to the control mixture and to the standard mixture; measuring area under an oxygen uptake curve of the control mixture and the standard mixture; and determining antioxidant activity in Trolox equivalents to provide a measure of the antioxidant activity of the test sample. The test sample may comprise either water-soluble ingredients or lipid-soluble ingredients, or both water-soluble and lipid-soluble ingredients.

A method of measuring stability of an antioxidant composition over time, the composition having water and lipid-soluble ingredients, by measuring oxygen uptake of the composition at a first time point and at a second, later, time point, is an embodiment of the present invention. The method comprises combining an oxidizable target molecule and the antioxidant composition in a solvent of acetone/water/detergent to form a test mixture at 37° C. under conditions where oxygen is present in equilibrium with air; adding an azo radical initiator to the test mixture; and measuring area under an oxygen uptake curve of the test mixture to provide a measure of the antioxidant activity of the antioxidant composition at the first time point and at the second time point, wherein a difference between the area under the oxygen uptake curve for the first time point and the area under the oxygen uptake curve for the second time point is a measure of stability of the antioxidant composition over time.

A further embodiment of the invention is a process of formulating an antioxidant composition having time release and increased shelf life. The process comprises blending the antioxidant composition of the present invention with a carrier comprising gum acacia, xanthan gum, gum tragacanth, gum ghatti, and aloe vera gel extract in a weight ratio of 30/30/20/19/1; wherein the composition and carrier have a weight ratio of 1:2 to 2:1 to form a blend; roller compacting the blend to form a compact; milling the compact to form a granulation; and forming the granulation into a dosage form.

A process of increasing the shelf life of an antioxidant formulation is an aspect of the present invention. The process comprises combining the antioxidant formulation and a carrier comprising gum acacia, xanthan gum, gum tragacanth, gum ghatti, and aloe vera gel extract in a weight ratio of 30/30/20/19/1; wherein the composition and carrier have a weight ratio of 1:2 to 2:1 to form a blend; and roller compacting the blend to form a compact.

A method of increasing serum antioxidant activity of an individual comprising administering 500 mg to 1 g of the antioxidant composition of the present invention per day to the individual is a further aspect of the present invention. An increase of up to 36.5% in antioxidant activity, as indicated by serum ORAC β-PE values, was observed by supplementation of the diet of individuals using the composition provided herein.

BRIEF DESCRIPTION OF THE DRAWINGS

FIG. 5 shows an HPLC chromatogram designed to examine flavonoid components of the Australian bush plum (*Terminalia ferdinandiana*). The chromatogram is from a reverse phase $C_{18}$ column using a stepped gradient of 0.1% trifluoroacetic acid and 100% methanol, at a flow rate of 1 mL/min using a sample of methanol and water-extracted bush plum powder. The conditions were developed to separate out flavonoids and vitamin C. The absorbance was measured at 245 nm. A peak corresponding to vitamin C is indicated, as well as a peak that is due to solvent.

DETAILED DESCRIPTION OF THE INVENTION

Figure 1:
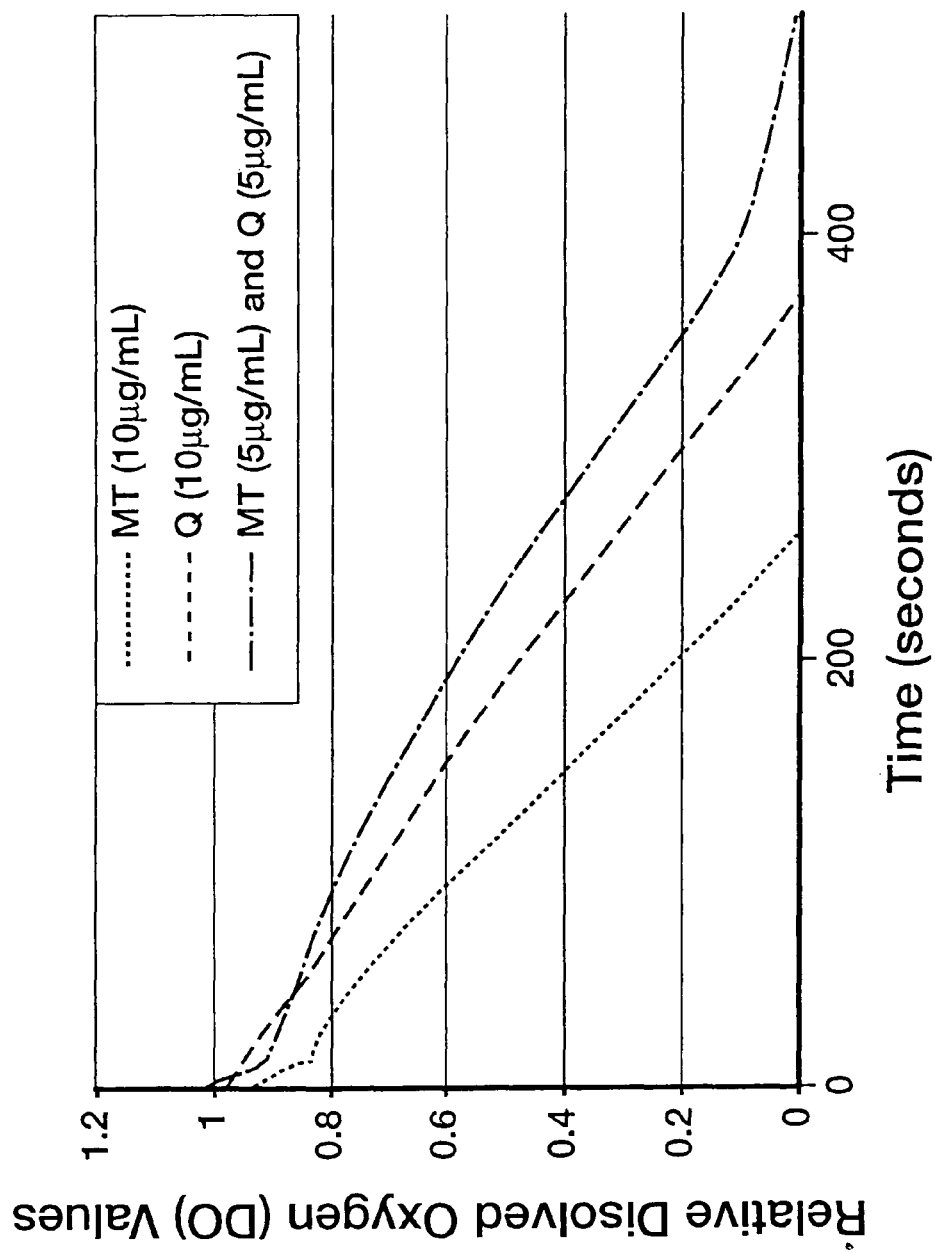
FIG. 1 shows an antioxidant effect of the combination of quercetin (Q) at 5 µg/mL and mixed tocopherols (MT) at 5 µg/mL as compared to each ingredient separately at a concentration of 10 µg/mL as measured by the ORAC(o) method of the present invention.

The present invention provides a performance assay that measures the oxygen radical absorption capacity (ORAC) of a composition comprising hydrophobic and/or hydrophilic antioxidants. The term ORAC(o) is used since the assay measures the ability of antioxidants to quench radicals by directly tracking the disappearance of oxygen. Current industry standard assays (ORAC(fl) and ORAC(β-PE)) measure antioxidant capacity by indirectly measuring degradation of a fluorescent compound (fluorescein or β-phycoerythrin) as marked by the disappearance of fluorescence. These assays work well with hydrophilic antioxidants, but have limited effectiveness in measuring hydrophobic antioxidants or mixtures of hydrophobic and hydrophilic antioxidants.

Since human cells require both hydrophobic and hydrophilic antioxidants, a method that directly and effectively measures the antioxidant activity of both in one assay as presented herein is desirable and an improvement over the presently used assays.

Antioxidants can act by scavenging reactive free radicals or other reactive oxygen species such as $O^{2\bullet}-$, $H_2O_2$, HOCl, ferryl, peroxyl, peroxynitrite, or alkoxyl, for example, or by preventing their formation, or by converting the free radical or other reactive oxygen species to a less reactive species.

Components of the ORAC(o) assay for antioxidant activity of the present invention are as follows.

Radical Initiator: Azo radical initiators are present in the ORAC(o) assay of the present invention at a concentration such as to generate radicals for measurements of antioxidant activity. Azo initiators include, for example, 2,2'-azobis[2-(5-methyl-2-imidazolin-2-yl)propane]dihydrochloride, 2,2' azobis (2-amidinopropane)dihydrochloride (AAPH), 2,2'-azobis(2-amidinopropane)[2-(N-stearyl)amidinopropane] dihydrochloride (SA-1), 2,2'-azo(2-(2-imidiazolin-2-yl)-propane)-[2-[2-(4-n-octyl)imidazolin-2-yl]-propane] dihydrochloride (C-8), 2,2'-azobis(4-methoxy-2,4-dimethylvaleronitrile) (MeO-AMVN), 2,2'-azobis(2,2'-azobis (2,4-dimethylvaleronitrile) (AMVN), azo-bis-isobutylnitrile, 2,2'-azobis (2-methylproprionate) (DAMP), and 2,2'-azobis-(2-amidinopropane).

In one embodiment of the assay, the radical generator is 2,2' azobis (2-amidinopropane) dihydrochloride (AAPH). Decomposition of AAPH produces molecular nitrogen and two carbon radicals. The carbon radicals may combine to produce stable products or react with molecular oxygen to give peroxyl radicals. The half life of AAPH is about 175 hours (37° C. at neutral pH). Therefore, the rate of free radical generation is essentially constant during the first several hours in solution. AAPH is used effectively for lipid peroxidation in aqueous dispersions of fatty acids.

Target Molecules: Linoleic acid is the target oxidizable molecule for the ORAC(o) assay. Further unsaturated fatty acids, including polyunsaturated fatty acids (PUFA's), having a carbon chain length of 6 to 20 carbons may be substituted for linoleic acid. AAPH will oxidize linoleic acid, as well as any other oxidizable compound in the system including the antioxidant being tested. The assay measures the ability of various antioxidants to protect against the AAPH-induced free radicals.

Solvent System: While the solvent system for the initial extraction with the prior art ORAC(fl) method involves putting 500 mg of sample in 20 mL of one-half acetone and one-half water (25 mg/mL), followed by dilutions with buffer, the solvent system for the ORAC(o) involves dissolving samples in one-third acetone, one-third water, and one-third detergent ("one-third" solvent) at a concentration of 1 mg/ML. Dilutions are then made using the same solvent. The detergent may be a nonionic detergent such as TWEEN®, (i.e., TWEEN®20), BRIJ®, or TRITON®; a zwitterionic detergent such as CHAPS®; a cationic detergent; or an anionic detergent such as cholate, deoxycholate, sodium dodecylsulfate, or TWEEN®-80; or a surfactant. The ratio of water to acetone to detergent may vary by up to about 10%.

Applications of the ORAC(o) Assay of the Present Invention: The ORAC(o) assay may be used to measure the total antioxidant activity for serum, lipid-soluble serum fraction, water-soluble serum fraction, urine, lipid-soluble urine fraction, water-soluble urine fraction, LDL fraction, tissue homogenates, quality control of antioxidant supplements, food products, or preservatives, development of new antioxidant supplements, development of new food products, new preservatives, or new antioxidant therapies, quality control of food manufacturing and processing, assessing antioxidant activity of plants, or monitoring the antioxidant activity of cosmetic products, for example.

The assay of the present invention is also provided for determining a condition under which an antioxidant may have activity of a pro-oxidant, i.e., the antioxidant is present under conditions where it promotes oxidation of a target rather than delaying or preventing oxidation of a target molecule. A pro-oxidant has a negative ORAC(o) value.

Components of the Synergistic Antioxidant Composition of the Present Invention: Using the performance antioxidant assay of the present invention, an antioxidant composition having synergistic activity is provided that includes flavonoids such as quercetin, a mixture of at least two forms of vitamin E, and optionally, grape skin extract, green tea extract and bush plum. The synergism is particularly observed in a weight ratio of quercetin to the mixture of vitamin E forms of 40/60 to 90/10%. One embodiment of the composition includes the following weight ratios: quercetin, 49.18%; mixed tocopherols, 32.79%; grape skin extract, 9.84%; green tea extract, 6.56%; and bush plum, 1.64%.

Flavonoids such as Quercetin: The flavonoid of the composition can be a flavone, a flavonol, an isoflavone, an isoflavonol, an analogue thereof, a pharmaceutically acceptable salt thereof, or a mixture thereof. Examples of a flavonol include quercetin, kaempferol, and myricetin. The particular flavonoid or flavonoid analogue or salt included in the composition is determined by running an ORAC(o) antioxidant determination. An activity within 80% percent of that of quercetin is contemplated to provide an analogue. Reference to a flavonoid, in particular, quercetin, also is intended to refer to the aglycone or a glycoside thereof where the sugar is arabinose, rhamnose, galactose or glucose, for example. The rhamnose glycoside of quercetin is known as rutin or quercetrin, and the rhamnose glycoside of myricetin is known as myricitrin. Analogues of quercetin include those compounds which comprise a substituting group other than an —OH group at one or more of the positions 3, 5, 7, 3', and 4'. Other substituting groups include: alkyl less than 5 carbon atoms, acetyl, sulphyl, or malonyl. For analogues of quercetin, only one or two of the positions are substituted with anything other than —OH groups.

A "pharmaceutically acceptable salt" is a salt of a flavonol with an organic or inorganic acid generally accepted as safe for oral consumption. Acid addition salts include chlorides, bromides, sulfates, nitrates, phosphates, sulfonates, formates, tartrates, maleates, malates, citrates, benzoates, salicylates, ascorbates, and others known to those of ordinary skill in the art.

Flavonoids such as quercetin are readily synthesised in vitro. However, flavonoids (including quercetin) are present and are prepared from naturally occurring foodstuffs, in particular, fruits and vegetables, such as apples, pears, grapes, onions, red wine, bell peppers, red currants, black currants, lemons, cherries, cranberries, gooseberries, tomatoes, olives, radishes, kohlrabi, horseradish, potatoes, and asparagus. Quercetin can be obtained from Pharnline (Florida, N.Y.).

A Mixture of at least Two Forms of Vitamin E: By "a mixture of at least two forms of vitamin E" is meant herein a mixture of at least two forms of tocopherol selected from alpha, beta, delta, epsilon, gamma, zeta, eta, xi1, xi2, and sigma tocopherols, and alpha, beta, delta and gamma tocotrienols, and combinations or derivatives thereof. In one embodiment, "a mixture of at least two forms of vitamin E" is a mixture of at least two forms of tocopherol selected from alpha, beta, delta, and gamma tocopherol. In another embodiment, "a mixture of at least two forms of vitamin E" is a mixture of alpha, beta, delta, and gamma tocopherol. "A mixture of at least two forms of vitamin E" may be obtained from VITAECAPS, SA, Spain, from Henkel Corporation; or from Cognis Corporation (Kankakee, Il.), for example. COVITOL® F-350M is commercially available from Cognis and contains natural source alpha-tocopherol with mixed tocopherols which are obtained from edible vegetable oils. The particular mixture of tocopherols included in the antioxidant composition of the present invention is determined by running an ORAC(o) antioxidant determination. An activity within 80% percent of that of mixed tocopherols of the present invention is contemplated to provide "a mixture of at least two forms of vitamin E."

Salts or derivatives of tocopherols include pharmaceutically acceptable salts such as acetate, sulfate, succinate, nicotinate, allophanate, phosphate, quinone, or halogenated derivatives; esters; stereoisomers; and the like. The invention encompasses the use of vitamin E derivatives in which substitutions, additions, and other alterations have been made in the 6-chromanol ring and/or side chain, with the proviso that the derivatives maintain antioxidant activity of a vitamin E. For example, tocopherols and their derivatives can vary by the number and position of alkyl groups, double bonds and other substituents and variations on the ring and side chain. An "alkyl" is a cyclic, branched or straight chain chemical group containing only carbon and hydrogen, such as methyl, butyl, and octyl. Alkyl groups can be either unsubstituted or substituted with one or more substituents, e.g., halogen, alkoxy, acyloxy, amino, hydroxyl, mercapto, carboxy, or benzyl. Alkyl groups can be saturated or unsaturated at one or several positions. Typically alkyl groups will comprise 1 to 8 carbons, 1 to 6, or 1 to 4 carbon atoms. Additional tocopherols can be constructed by conjugation to the ring structure or side chain of various other moieties, such as those containing oxygen, nitrogen, sulfur and/or phosphorus. Tocopherol derivatives can also be made by modifying the length of the side chain from that found in prototypical tocopherols such as alpha-, beta-, delta- and gamma-tocopherol. Tocopherols can also vary in stereochemistry and saturation of bonds in the ring structure and side chain.

Additional tocopherol derivatives, including prodrugs, can be made by conjugation of sugars or other moieties to the side chain or ring structure. Mixed tocopherols include without limitation mixtures of stereoisomers of a single tocopherol (e.g., + and − stereoisomers of alpha-tocopherol; (+/−) indicates a racemic mixture) or mixtures of structurally distinct tocopherols (e.g., alpha-plus gamma-tocopherol).

Bush Plum: The Australian bush plum (*Terminalia ferdinandiana*) contains about 5% vitamin C and a variety of ingredients as demonstrated by an HPLC chromatogram at FIG. 5. These ingredients are believed to include flavones, and flavonoids. The HPLC chromatogram is from a reverse phase $C_{18}$ column using a stepped gradient of 0.1% trifluoroacetic acid and 100% methanol, at a flow rate of 1 mL/min using a sample of methanol and water-extracted bush plum powder. The conditions were developed to separate flavonoids and to separate vitamin C. The absorbance was measured at 245 nm.

Pulp and skin of a bush plum are removed from the seed of the fruit and made into a slurry in water. The slurry is freeze-dried and ground. For antioxidant compositions herein, the freeze-dried material is weighed in the desired amount. Bush plum is present in the composition of the present invention in an amount of from 0% to 87.9%, or in another embodiment, about 2% by weight.

Grape skin extract: Grape skin extract is made from grape skins, and contains 30-82% polyphenols and may be obtained from Polyphenolics, Madera, Calif.; Hunan Kinglong, Bio-Resource Co. Ltd, Changsha Economic Development Zone, China; or from Pharmline, Florida, N.Y.

Green tea extract: Green tea extract is an extract from the leaves of *Camellia sinensis*, contains 35-95% polyphenols, and may be obtained from Amax NutraSource Inc., Eugene, Oreg.; Blue California, Rancho Santa Margarita, Calif.; or from PL Thomas & Co., Morristown, N.J.

Other Ingredients: Antioxidant compositions of the present invention may comprise a non-toxic, pharmaceutically acceptable carrier such as lactose, starch, sucrose, glucose, methyl cellulose, magnesium stearate, dicalcium phosphate, calcium sulfate, mannitol, sorbitol, cyclodextrin, cyclodextrin derivatives, or the like. Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tablets may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

Capsules or tablets may optionally be coated or scored and may be formulated so as to provide slow- or controlled-release of the antioxidant composition. Timed-release compositions for controlled release of agents generally contain agent particles mixed with or coated with a material that is resistant to enteric degradation or disintegration for a selected period of time. Release of the agent may occur by leeching, erosion, rupture, diffusion or similar actions.

Carriers may promote antioxidant stability as well as providing time release. A mixture of plant carbohydrates termed AMBROTOSE® Phyto Formula may be combined with the antioxidant composition. Such a combination extends the shelf life of the antioxidant composition and provides for a time release form. AMBROTOSE® Phyto Formula contains, in a weight/weight ratio of about 30/30/20/19/1, gum Arabic (acacia), xanthan gum, gum tragacanth, gum ghatti, (which may be obtained from TicGum) and aloe vera gel extract (inner leaf gel, Carrington Labs, Irving, Tex., Manapol® powder). The AMBROTOSE® Phyto Formula is blended with the antioxidant composition of the present invention in a weight ratio of 2:1 to 1:2. In another embodiment, AMBROTOSE® Phyto Formula is blended with the antioxidant composition in a weight ratio of 2:1.

Capsules or tablets may contain further plant components in trace weight percentages less than 0.1%, the components having no essential significance to the composition.

Formulation Processes: A process of formulating a roller compacted antioxidant composition comprises blending AMBROTOSE® Phyto Formula with the antioxidant composition set forth herein. The resultant blend is transferred to a roller compactor and compacted between rollers to form a compact. The pressure imparted on the blend enhances the physical adhesion between the ingredients. The compact is subsequently milled to form a granulation. The resultant granulation is then formed into the desired dosage form, such as capsules or tablets. A Fitzpatrick Chilsonator Model 4LX10D roller compactor was used herein, having rolls that are notched across the face and perpendicular to the rotation, having a fixed force of 10 ton, and a Fitzmill screen of 0.093. The roller compaction device may have variable rotation speed, force application, and gap width capabilities, for example, a Gerteis Polygran dry roller compactor system (Gerteis, Germany). The roller compactor functions by uniformly applying pressure on a blend by passing the blend between two counter-rotating rollers. The pressure imparted on the blend by the rollers compresses the blend into a compact, such as a sheet or ribbon, which is typically milled to produce granules. Alternatively, granulation may be achieved by slugging, milling or sieving as may be required. Granules having a mesh of #20-80 are desired.

A longer shelf life of the roller compacted combination of the antioxidant composition with AMBROTOSE® Phyto Formula is believed due to the reduction in the amount of surface area of the antioxidant composition exposed to oxygen. The roller compacted combination also eliminates the need for excipient fillers in the capsule or tablet-making process. Additional benefits of a combination of AMBROTOSE® Phyto Formula with the antioxidant composition set forth herein include: provision of non-soluble fiber which may serve as a sink for unpaired electrons in the gut, and provision of monosaccharides for correct structure of cellular glycoforms responsible for cell-mediated communication in repair of cells damaged by free radicals.

Dosage: Useful dosage formulations for administration of the compositions of the present invention include capsules or tablets of 100, 200, 300, 400, 500, 600, 700, 800, 900 or 1000 mg of antioxidant composition. In one embodiment, no fillers, carriers, or stabilizers are added to the composition. In another embodiment, AMBROTOSE® Phyto Formula is blended with the antioxidant composition of the present invention in a weight ratio of 2:1, 1:1, or 1:2. In another embodiment, AMBROTOSE® Phyto Formula is blended with the antioxidant composition in a weight ratio of 2:1. In another embodiment, a capsule or tablet provides 500 mg of antioxidant composition blended with AMBROTOSE® Phyto Formula. For this embodiment, two tablets or capsules may be taken per day. Appropriate coatings may be applied to increase palatability or delay absorption.

EXAMPLE 1

Comparison of Antioxidant Activity Using ORAC(fl) and ORAC(o) Assays

Ingredients for an antioxidant composition were analyzed for antioxidant activity using a prior art oxygen radical absorption capacity method that measures flouresence (ORAC(fl)), and using the method of the present invention that measures dissolved oxygen (ORAC(o)). The antioxidant activity of a product is its ability to protect the system from damage caused by peroxyl radicals.

Prior Art Method of Measuring Antioxidant Activity for Comparison: For the ORAC(fl) assay, the method of Ou et al. (Ou, B., Hampsch-Woodill, M. and Prior, R. L., *J. Agric. Food Chem.* 2001, 49, 4619-4626) was followed. Differences from the Ou procedure as published included the speed of the orbital shaker (Ou, 400 rpm; herein, 280 rpm), and the centrifuge speed (Ou, 14,000 rpm, 15 min; herein, 3200 rpm, 15 min and the length of the assay (Ou, 30 min; herein, 100 min). Fluorescein, sodium salt, was obtained from Aldrich (Milwaukee, Wis.). For the Ou method, a standard amount of fluorescein is added to an antioxidant product being tested, and the beginning level of fluorescence is measured. A free radical initiator is added, and the time and degree of disappearance of fluorescence are measured. Trolox, a synthetic antioxidant with a structure similar to vitamin E (i.e. a structure similar to a strong antioxidant which is consistent from lot-to-lot), is used as the standard and run for comparison with each sample. A blank (control) is also included in each run. Fluorescence vs. time is plotted. The blank (control) is subtracted from every curve. The net area under the curve of the antioxidant is compared to the net area under the curve of Trolox. The larger the net area under the curve, the better the antioxidant. All ORAC(fl) analyses were performed on a COBAS FARA II centrifugal analyzer (Roche Diagnostic System Inc., Branchburg, N.J.; excitation wavelength=493 nm and emission filter=515 nm). Results are given as micromoles of Trolox equivalents per gram of sample.

Method of Measuring Antioxidant Activity of the Present Invention: For the ORAC(o) assay of the present invention, the antioxidant product being tested is added to a solution containing a target molecule (linoleic acid) with oxygen present at equilibrium with the air. Then a free radical initiator is added, and the time it takes the oxygen to disappear is measured, yielding the rate of disappearance. Trolox is used as the standard, and a blank is run as a control. Amount of dissolved oxygen vs. time is plotted allowing direct comparison of net areas under the curve. A detailed method is as follows:

Buffers ($K_2HPO_4$(F. W. 174.2), $NaH_2PO_4$(F W 120.0)) were obtained from Sigma (St. Louis, Mo.). Linoleic acid 99%, Trolox (6-hydroxy-2,5,7,8-tetramethylchroman-2-carboxylic acid) 97%, TWEEN® 20, and 2,2'-azobis (2-methylpropionamidine) dihydrochloride 97% (AAPH), were obtained from Aldrich (Milwaukee, Wis.). HPLC grade acetone was obtained from Fisher (Hampton, N.H.). A YSI 5300A biological oxygen meter was obtained from YSI (Yellow Springs, Ohio) and used according to the manufacturer's specifications.

Samples were prepared at a concentration of 1 mg/mL in "one-third" solvent. "One-third" solvent is equal parts of water, acetone, and a solution of TWEEN®20 diluted 1:9 with water. Samples were shaken for 1 hour at room temperature on an orbital shaker at 280 rpm. The sample solution was ready for analysis after further dilution (generally to 10 μg/mL) with "one-third" solvent. "One-third" solvent was also used as the blank.

The ORAC(o) assay was carried out using the YSI 5300A biological oxygen meter. Linoleic acid was prepared by adding 0.18 mL of 75 mM phosphate buffer (pH 7.4), 0.18 mL of 10 weight percent TWEEN®20 stock solution, and 0.44 mL of deionized water to 70.8 mg linoleic acid. AAPH was prepared by adding 0.9 mL of buffer to 67.8 mg of AAPH. In the final reaction volume (5.218 mL), linoleic acid (21.59 mM) was used as the target of free radical attack, and AAPH (19.00 mM) was used as a peroxyl radical generator. Trolox (at 10 μg/mL) was used as a standard. Readings were taken every second until a zero reading was observed.

The formula for calculating the ORAC(o) value (Oxygen Radical Absorbance Capacity oxygen specific electrode) is:

$$ORAC(o) = \frac{\frac{AUC_{SMP} - AUC_{BLNK}}{AUC_{TRLX} - AUC_{BLNK}} \times 1000 \times [TRLX \text{ (}\mu\text{mol/ml)}]}{[SMP \text{ (mg/ml)}]}$$

This calculation yields a quantity known as micromoles of Trolox equivalents per gram of sample. As used herein the terms "relative ORAC(o)" and "ORAC(o)" refer to the same value. A negative value reflects less radical quenching activity than obtained with a blank which indicates that a composition is a pro-oxidant, i.e., an agent that promotes oxidation, rather than acting as an antioxidant.

Comparison of ORAC(o) and ORAC(fl) Assay Parameters:

A comparison of the assay parameters of the ORAC(fl) and the ORAC(o) methods is provided in Table 1.

under the ORAC (fl) conditions is what made up an ORAC(fl) sample, and a supernatant solution made according to the ORAC(fl) method for analysis may not be representative of the actual sample. Since a solution of a sample in the ORAC (fl) buffer does not always reflect the contents of the sample, results can be skewed using the ORAC(fl).

Figure 4:
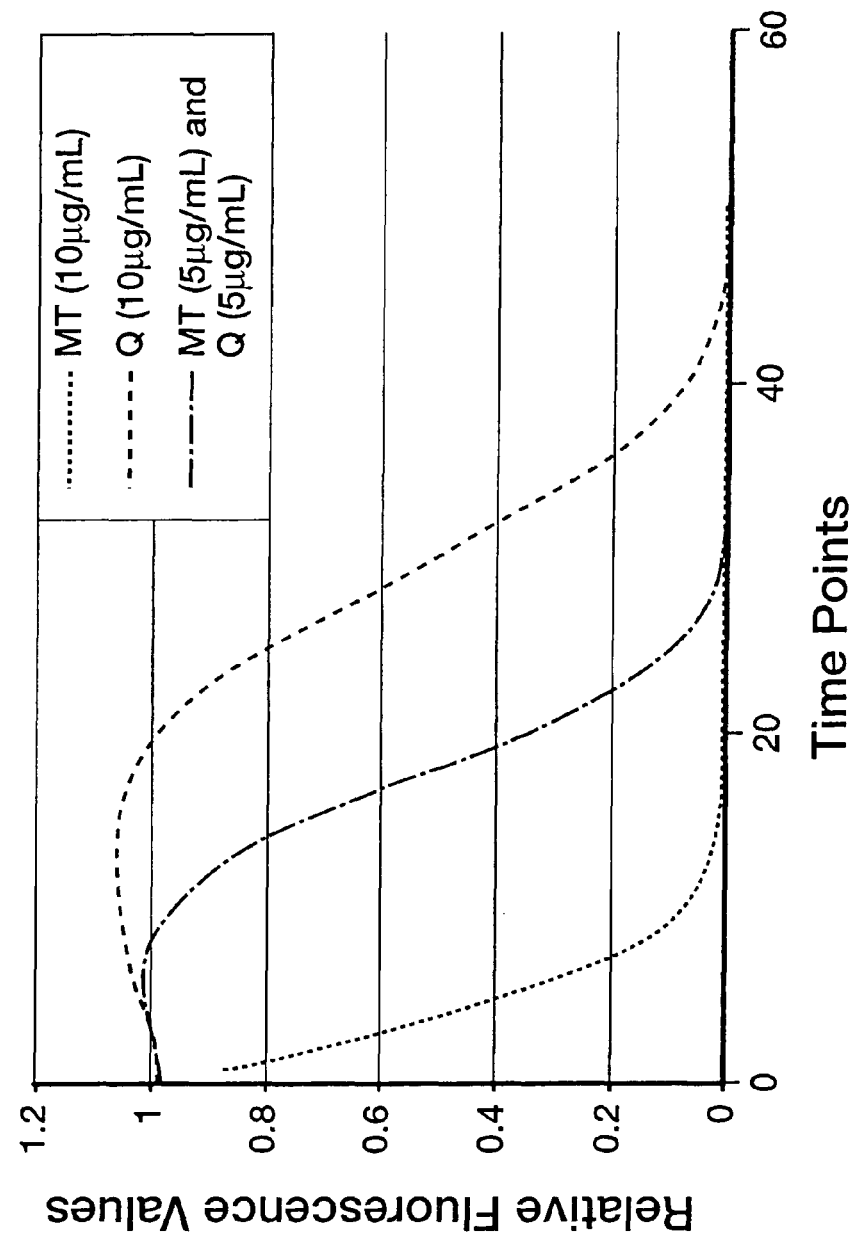
FIG. 4 shows ORAC(fl) results of the combination of quercetin (Q) at 5 µg/mL and mixed tocopherols (MT) at 5 µg/mL as compared to each ingredient separately at a concentration of 10 µg/mL.

The problem with sample dissolution was recognized and a lack of contribution of mixed tocopherols to an antioxidant measurement carried out on a mixture of quercetin and mixed tocopherols when using the ORAC(fl) was observed. FIG. 1 shows that the ORAC(o) demonstrates an antioxidant effect of the combination of quercetin at 5 µg/mL and mixed tocopherols at 5 µg/mL as compared to each ingredient separately at 10 µg/mL. In contrast, FIG. 4 shows that the ORAC(fl) shows no further effect from the same combination beyond the value for quercetin alone. Lack of activity from such a

TABLE 1

| Assay Parameter During Assay | ORAC(fl) | ORAC(o) |
|---|---|---|
| Temperature | 37° C. | 37° C. |
| AAPH concentration | $1.28 \times 10^{-2}$ M in phosphate buffer | 19.00 mM in phosphate buffer |
| Target molecule concentration | fluorescein, 43.8 nM in phosphate buffer | 21.59 mM linoleic acid, in mixture of 10% TWEEN ® 20, buffer and water (.18 mL, .18 mL, .44 mL) |
| Sample concentration | initially at 500 mg in 20 mL, supernatants diluted to 10 µg/mL with buffer | 1 mg/mL initially, diluted to 10 µg/mL |
| Sample solvent | acetone/water, 50/50 v/v dilutions in phosphate buffer | water/acetone/10% by weight TWEEN ® 20, v/v/v ("one-third" solvent) dilutions in "one-third" solvent |
| Buffer for assay, concentration | 75 mM phosphate, pH 7.4 | 75 mM phosphate, pH 7.4 |
| Final assay volume | 400 µl | 5.218 mL |
| Blank (control) | buffer | "one-third" solvent |
| Standard | 62.5 µM Trolox in buffer | Trolox at 10 µg/mL (38.755 µM) in "one-third" solvent |
| Method of measuring antioxidant capacity of the sample | fluorescein yields a decrease in fluorescence as it is oxidized by radicals, antioxidant protects and delays decrease | oxygen is taken up by the radical initiator, and by linoleic acid carbon radicals; antioxidant protects and decreases oxygen uptake |

Advantages of the ORAC(o) as Compared to the ORAC (fl):

Direct vs. Indirect Measurement of Antioxidant Potential: The ORAC(fl) is an indirect method in that it relies on the assumption that the fluorescein (target molecule) is the only fluorescent component being measured. However, many antioxidant compounds fluoresce naturally (e.g. blueberries); and combinations of these compounds from radical-radical reactions fluoresce also. Fluorescence from the sample, therefore, can skew the results of an assay based on fluorescence. The ORAC(o) method, on the other hand, is a direct measurement of oxygen uptake, a direct measurement of the disappearance of oxygen into free radicals. This method of measurement of antioxidant capacity is not dependent upon whether the oxygen is attched to water- or lipid-soluble components.

Saturation of Samples: Ou et al. prepared samples in acetone/water (50:50, v/v) at a concentration of 500 mg in 20 mL, rotated them on a rotary shaker at 400 rpm for 1 hour, centrifuged them at 14,000 rpm for 15 minutes, and diluted them with 75 mM potassium phosphate buffer at pH 7.4. The present inventors found that much of a test sample would not go into solution under the Ou conditions (ORAC(fl) conditions), the more soluble components displace the less soluble components. Consequently, only that which was solubilized combination with mixed tocopherols and saturation problems are absent from the ORAC(o) method since the concentration of sample is more dilute and since the solvent for the sample contains acetone, water, and a detergent for solubilizing all components of a sample. Presence of TWEEN®20 in the solvent for the sample accounted for detection of activity from mixed tocopherols.

Automation: The ORAC(fl) method is automated (Cobas Fara II by Roche Diagnostic Systems), which provides the ability to run numerous samples at once and minimizes potential for human error. The ORAC(fl) method can also be performed using a fluorometer without automation. Since the ORAC(o) method is not yet automated, it is more labor intensive at the present time, however, the ORAC(o) method is expected to be automated.

Expense: A new, automated machine capable of running the ORAC(fl) can cost $250,000; a non-automated fluorometer costs about $50,000; the ORAC(o) method, which uses an oxygen-specific electrode, can be set up for only several hundred dollars.

Precision of Results: In the present assays, the fluorometer appeared to provide more precise results than the oxygen probe, possibly because it is automated.

Validation: Validation, as conducted by the Association of Official Analytical Chemists (AOAC) guidelines for single laboratory validation provided results in Tables 2, 3, and 4.

TABLE 2

5 Day Trial for Precision (Repeatability)

| | Area under Curve |
|---|---|
| Day 1 | 202.655447939563 |
| Day 2 | 212.901122995373 |
| Day 3 | 187.01466464995 |
| Day 4 | 202.856617129109 |
| Day 5 (2$^{nd}$ Analyst) | 213.124092629655 |
| 5 Day Mean | 203.710389068730 |
| Standard Deviation | 10.649840914564 |
| Relative Standard Deviation | 5.23% |
| HORRAT | 1.981060606061 |

The values for each day are an average of 3 runs of the quercetin sample at a concentration of 10 μg/mL. The HORRAT value is the ratio between observed $RSD_R$ values and the $RSD_R$ values predicted by the Horwitz equation known to those of skill in the art, and is regarded as an indication of the acceptability of a method with respect to its precision. In a single laboratory performance study, a series of HORRAT ratios between 0.5 and 2.0 indicate acceptable precision of a method. The HORRAT value for the 5-day trial is 1.98.

A determination of the analytical range as a linear range is provided in Table 3.

TABLE 3

Determination of Analytical Range

| Sample (μg/ml) | Area Under Curve |
|---|---|
| 1 | 124.567114093960 |
| 10 | 209.388111888112 |
| 100 | 693.611111111111 |
| 500 | 2327.96518987343 |
| 1000 | 2870.09540636041 | y=2.8335x+332.16; $R^2$=0.9231 for 1-1000 plot
y=4.3353x+176.66; $R^2$=0.9967 for 0-500 plot Linear integrity appears to decline as the sample concentration nears 1000 μg/mL. With the determination of the analytical range as a linear range, the value of the area under the curve of variable concentrations up to 500 μg/mL is determined.

Table 4 provides results for precision of single-day results.

TABLE 4

Single Day Trial for Precision (Repeatability)

| | Area under curve |
|---|---|
| Run 1 | 207.369402985075 |
| Run 2 | 198.18118466899 |
| Run 3 | 205.035211267606 |
| Run 4 | 201.586572438162 |
| Run 5 | 202.110714285714 |
| 5 Run Mean | 202.856617129109 |
| Standard Deviation | 3.505016471434 |
| Relative Standard Deviation | 1.73% |
| HORRAT | 0.654480870834 |

The single day precision trial involved 5 separate runs of the quercetin sample at a concentration of 10 μg/mL. The HORRAT value of Table 4 for the ORAC (o) method is 0.65448.

Accuracy: The ORAC(o) is believed by the present inventors to be more accurate than the ORAC(fl) for the reasons stated herein.

Results: The ORAC(o) assay was used to optimize ratios of the ingredients in an antioxidant composition as set forth in Example 2. One embodiment of the composition having weight ratios of quercetin, 49.18%; mixed tocopherols, 32.79%; grape skin extract, 9.84%; green tea extract, 6.56%; and bush plum, 1.64% gave an antioxidant value using the ORAC(o) of 17,254 micromoles Trolox equivalents per gram. The same composition gave an antioxidant value using the ORAC(fl) of 5,281 micromoles Trolox equivalents per gram. These data demonstrate that the ORAC(o) and ORAC (fl) methods of measuring antioxidant activity differ in the results obtained. The inventors of the present invention believe that the ORAC(o) method is preferred for the reasons stated supra.

EXAMPLE 2

A Synergistic Antioxidant Composition

According to the present invention five ingredients were combined into an antioxidant composition, each of which is prominent in the diet of long-lived peoples from regions around the world. Flavonols, mixed tocopherols, grape skin extract, green tea extract, or bush plum are prominent in the diet of peoples of the Andean village of Vilcabamba in Ecuador, the land of Huza in the Karakoram Range in Kashmir, or in Abkhazia in the Georgian State of the former USSR, for example, as cited in Leaf A., Launois J. "A Scientist Visits Some of the World's Oldest People," *National Geographic*. 1973 January; of the Italian island of Sardinia (Koenig R. "Sardinia's Mysterious Male Methuselahs," *Science*. 2001, Mar. 16), and of Australia.

The present invention has demonstrated a synergistic antioxidant activity of the compositions of the present invention. Not wanting to be bound by theory, the present inventors believe the various ingredients of the antioxidant composition have activity for protecting intracellular cytosol, cellular membranes, and extracellular fluid such that the body is protected throughout. The bush plum component is high, for example, in natural vitamin C content, which can get into the cell, is hydrophilic, and is available for protecting the cytosol; the grape skin extract and green tea extract are hydrophilic, cannot enter the cell and are available for protecting extracellular fluid; and mixed tocopherols are lipophilic, and together with flavonols (e.g., quercetin), which are both hydrophilic and lipophilic, protect membranes.

Figure 2:
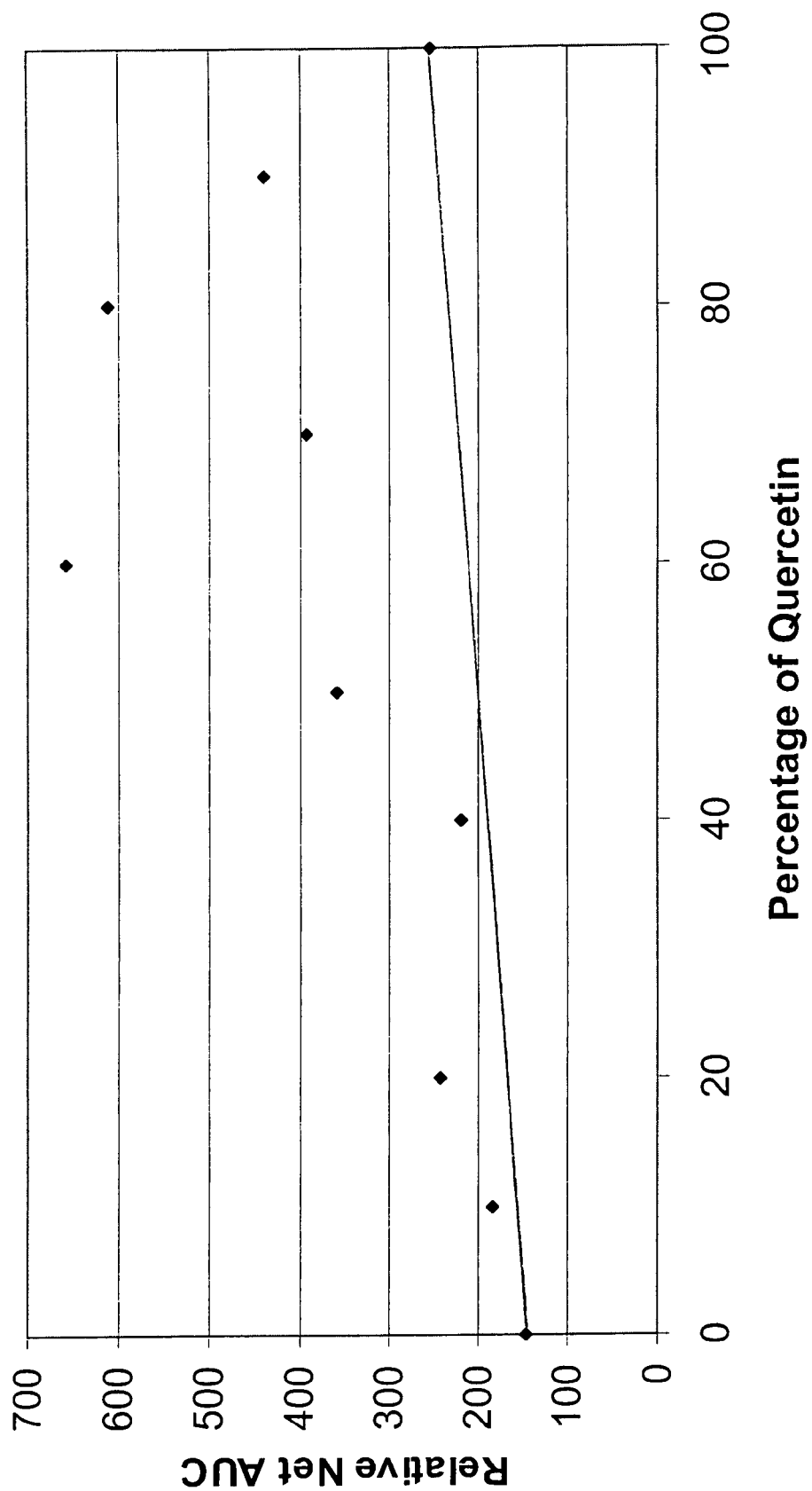
FIG. 2 shows area under the curve (AUC) results for varying ratios of quercetin and mixed tocopherols using the ORAC(o) method to measure antioxidant capacity. The total concentration of sample (Q+MT) is 10 µg/mL for each percentage assayed. For example, at 0% quercetin, the concentration of mixed tocopherols is 10 µg/mL, and there is no quercetin in the sample. At 10% quercetin, the sample has 1 µg/mL of quercetin and 9 µg/mL of mixed tocopherols. At 20% quercetin, the sample has 2 µg/mL of quercetin and 8 µg/mL of mixed tocopherols. The synergy is readily observed between 40 and 100% quercetin, and most readily from 40 to 90% quercetin. The straight line represents the additive effect, i.e., at 10% quercetin, the line represents the sum of 90% of the activity of mixed tocopherols alone and 10% of the activity of quercetin alone. A synergistic effect is found above this line.

FIG. 2 shows area under the curve (AUC) results for varying ratios of quercetin and mixed tocopherols using the ORAC(o) method to measure antioxidant capacity. The total concentration of sample (Q+MT) is 10 μg/mL for each percentage assayed. For example, at 0% quercetin, the concentration of mixed tocopherols is 10 μg/mL, and there is no quercetin in the sample. At 10% quercetin, the sample has 1 μg/mL of quercetin and 9 μg/mL of mixed tocopherols. At 20% quercetin, the sample has 2 μg/mL of quercetin and 8 μg/mL of mixed tocopherols. The synergy is readily observed between 40 and 100% quercetin, and most readily observed from 40 to 90% quercetin. The straight line represents the additive effect, i.e., at 10% quercetin, the line represents the sum of 90% of the activity of mixed tocopherols alone and 10% of the activity of quercetin alone. A synergistic effect is found above this line.

The primary ingredients of the composition of the present invention (flavonoids, as represented by quercetin, and a mixture of at least two forms of vitamin E) comprise from 12.1% to 100%, 30% to 85%, or in another embodiment, about 82% by weight of the five ingredients. In one embodiment, the amount of quercetin is 49.18% and the amount of vitamin E forms is 32.79% of the total weight of the five ingredients.

Figure 3:
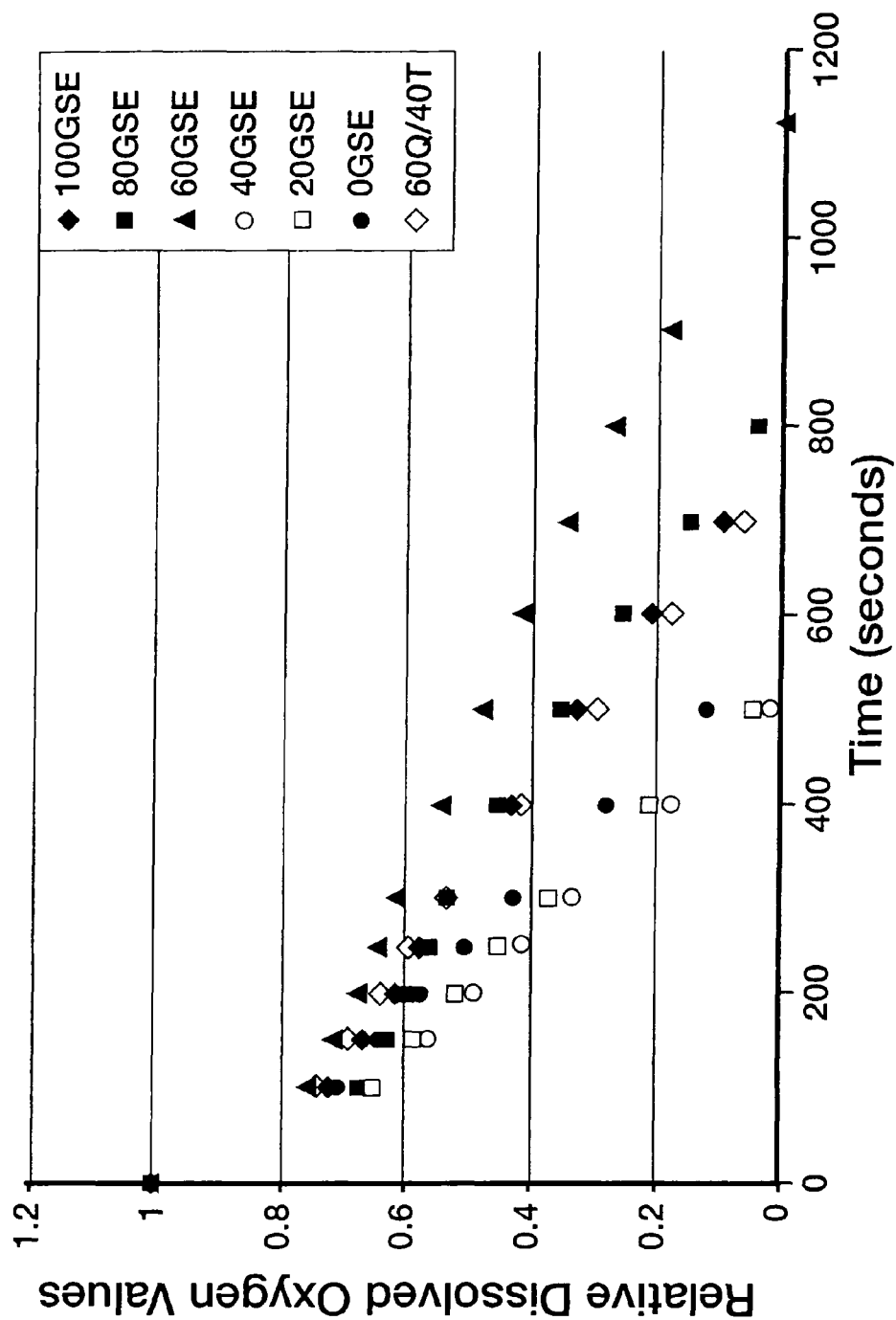
FIG. 3 shows ORAC(o) assays for varying ratios of grape skin extract and green tea extract in the presence of 49.18% quercetin, 32.79% mixed tocopherols, and 1.64% bush plum. The optimal ratio of grape skin extract to green tea extract is 60/40 to 80/20.

The secondary ingredients of the composition of the present invention (grape skin extract, green tea extract, and bush plum) comprise from 0% to 87.9%, 15% to 70%, or about 18% by weight of the five ingredients. The optimal ratio of grape skin extract and green tea extract was determined in the presence of 49.18% quercetin, 32.79% mixed tocopherols, and 1.64% bush plum as shown in FIG. 3. The optimal ratio of grape skin extract to green tea extract is 60/40 to 80/20. In one embodiment, the grape skin extract is 9.84% and the green tea extract is 6.56% of the total weight of the antioxidant composition.

Bush plum (*Terminalia ferdinandiana*) is provided as an ingredient of the composition in an amount from 0% to 87.9%, or in another embodiment, 2%. In the embodiment of FIG. 3, the bush plum is 1.64% of the composition.

The ORAC(o) assay shows that an antioxidant blend having the following weight ratios: quercetin, 49.18%; mixed tocopherols, 32.79%; grape skin extract, 9.84%; green tea extract, 6.56%; and bush plum, 1.64% has an antioxidant activity of 17,254 micromoles Trolox equivalents per gram.

EXAMPLE 3

Stability of AMBROTOSE AO™

At this writing, AMBROTOSE AO™, a blend of AMBROTOSE® and the antioxidant formulation of the present invention at a 2:1 weight ratio, has been shown to maintain its activity under accelerated stability conditions (40° C. at 75% relative humidity) equating to a shelf-life of roughly six months.

EXAMPLE 4

Antioxidant Effect of AMBROTOSE AO™ in Healthy Individuals

The present study was designed to determine the in vivo antioxidant activity of different amounts of Ambrotose AO™ as determined by serum ORAC($\beta$-PE) and urine lipid hydroperoxide analyses. Thirteen healthy male and female adult volunteers taking no nutritional supplements or any drug that would interfere with the study were enrolled. Twelve volunteers, ages 22-61, including 4 males and 8 females, consumed increasing amounts of the antioxidant supplement. Of those, six used tobacco products. Serum ORAC($\beta$-PE) values, indicators of oxidative protection, and urine lipid hydroperoxide levels, markers of oxidative damage, were chosen to assess subjects oxidative stress states. During the study participants continued their normal pre-study daily routines.

Subjects had morning fasting serum ORAC($\beta$-PE) and urine lipid hydroperoxide analyses performed after an initial washout period of 2 weeks (on no supplements) and at the end of 2 weeks on each of the amounts of the AMBROTOSE AO™. The amounts used were 500 mg (1 capsule) each day for the first 14 days of supplement use, 1 g (2 capsules) each day for the second 14-day period, and 1.5 g (3 capsules) each day during the third 14-day period. Serum samples were collected by a phlebotomist from Cover-Tek, Inc., an independent company in Dallas, Tex., and serum and urine samples were immediately packed in dry ice and shipped overnight for analysis by Genox Corporation, an independent laboratory in Baltimore, Md. All samples were stored in dry ice at Genox, and analyses were done at the same time at the conclusion of the study to minimize any analytical variability. Statistical analyses were performed by Decision Analyst, Inc., an independent firm in Arlington, Tex.

The precision of the analyses was tested by sending in a blinded control sample in triplicate. ORAC($\beta$-PE) values varied ±4.4%, staying well within the expected limits of the assay, and the hydroperoxide/creatinine values varied ±1.5%.

Average ORAC($\beta$-PE) in micromoles Trolox equivalents per gram at the end of each period for the twelve participants is as follows:

| | |
|---|---|
| end of washout period | 4280 |
| two weeks on 500 mg | 4898 |
| further two weeks on 1 g | 5841 |
| further two weeks on 1.5 g | 4815. |

A paired t-test was conducted to determine if there was a difference between the ORAC baseline data and the ORAC period 1 data. The baseline mean (4279.49) was significantly lower than the period 1 mean (4898.31) at approximately 90% confidence (p=0.094). A paired t-test also was conducted to test for a difference between the ORAC baseline and the ORAC period 2 data. The baseline mean (4279.49) was significantly lower than the period 2 mean (5841.08) at approximately a 99% confidence level (p=0.000).

Lipid hydroperoxide values in micromolar/(mg/dl) are corrected for urine concentration variability by dividing by urine creatinine as measured at the same time on the same sample and are as follows:

| | |
|---|---|
| end of washout period | .0920 |
| two weeks on 500 mg | .0808 |
| further two weeks on 1 g | .0782 |
| further two weeks on 1.5 g | .0764 |

A paired t-test was conducted to determine if there was a difference between the Lipid Hydroperoxide Creatinine baseline data and the Lipid Hydroperoxide Creatinine period 1 data. The baseline mean (0.0908) was not significantly higher than the period 1 mean (0.0817) (p=0.511). A paired t-test also was conducted to test for a difference between the Lipid Hydroperoxide Creatinine baseline and the Lipid Hydroperoxide Creatinine period 2 data. The baseline mean (0.0908) was not significantly higher than the period 2 mean (0.0775) (p=0.613).

Air quality is known to affect levels of oxidative stress. The poorer the air quality, the greater the oxidative stress. A summary of the average US Environmental Protection Agency (EPA) air quality index for each two-week period in the Dallas/Fort Worth area, which is where the subjects lived, is as follows (a value of 1.0 describes good air quality, a value of 2.0 describes moderate air quality, and a value of 3.0 is considered unhealthy for sensitive groups):

| | |
|---|---|
| end of washout period | 1.0 |
| two weeks on 500 mg | 1.0 |
| further two weeks on 1 g | 1.4 |
| further two weeks on 1.5 g | 1.8. |

Increased consumption of fruits and vegetables from the usual five to an experimental ten servings a day was found in a clinical study to significantly increase serum ORAC(β-PE) values by approximately 13% after two weeks (Cao et al., Am. *J Clin. Nutr*. 1998:68, 1081-1087). In the present study, the increase in average serum ORAC(β-PE) values using each amount of supplement were, 14.4% with 500 mg, 36.5% with 1.0 g, and 12.5% with 1.5 g. These data suggest that the optimum amount that results in the greatest rise in serum ORAC(β-PE) over baseline is 1.0 g. The percentage increase with 1.0 g is greater than the published 10% found by adding five fruits and vegetables to the diet.

The urine hydroperoxide/creatinine values decreased with increasing supplement use. Percentage decrease with each amount was 12.1% with 500 mg, 15.0% with 1.0 g, and 17.0% with 1.5 g suggesting that protection from lipid damage increased with increasing amounts of supplement over the range used.

The hydroperoxide data do not correlate exactly with the ORAC(β-PE) values in suggesting that 1.0 g is the optimal amount to use. Serum ORAC(β-PE) is a measure of the antioxidant protection of the blood in regard to its ability to quench free radicals at the time of the measurement. Urine lipid hydroperoxides are a marker of lipid oxidative damage at some time in the past. The temporal relationship between the actual lipid damage, and the appearance of hydroperoxides in the urine is not well-defined. It may well be that these temporal differences account, in part, for this variance.

Participants in the study lived in the Dallas/Ft Worth (DFW) area. The published EPA daily air quality assessments for DFW were averaged for each two week period. Air quality was, on average, getting worse over the course of the study. This would normally be expected to decrease oxidative protection, and hence ORAC(β-PE), and increase oxidative damage and urine lipid hydroperoxides. Yet, increased protection and decreased damage were evident, suggesting that the protection afforded by the supplement could have been greater than actually measured.

These data demonstrate that the present antioxidant supplement increases antioxidant protection in consumers as measured by serum ORAC(β-PE) and decreases lipid oxidative damage as measured by urine lipid hydroperoxides.

Those of skill in the art, in light of the present disclosure, appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. An antioxidant composition comprising:
   a flavonoid selected from the group consisting of a flavone, a flavonol, an isoflavone, an isoflavonol, an analogue thereof, a pharmaceutically acceptable salt thereof, and mixtures thereof; and
   a mixture of at least two forms of vitamin E selected from the group consisting of alpha, beta, delta, epsilon, gamma, zeta, eta, xi1, xi2, and sigma tocopherols, and alpha, beta, delta and gamma tocotrienols, and derivatives thereof;
   bush plum pulp and skin comprising 5% vitamin C;
   green tea extract comprising 35-95% polyphenols; and
   grape skin extract comprising 30-82% polyphenols;
   wherein the flavonoid and mixture of vitamin E forms are primary ingredients and the primary ingredients are present in the composition in an amount of from 30% to 85% by weight and act in synergy to provide a higher antioxidant capacity;
   wherein the bush plum pulp and skin, the green tea extract, and the grape skin extract are secondary ingredients and the secondary ingredients are present in the composition in an amount of from 15% to 70% by weight;
   wherein the flavonoid and the mixture of vitamin E forms are present in the composition in a weight ratio of from 40/60 to 90/10 percent; and
   wherein the grape skin extract and the green tea extract are present in the composition in a weight ratio of from 60/40 to 80/20 percent.

2. The antioxidant composition of claim 1 wherein the primary ingredients are present in the composition in an amount of 82% by weight.

3. The antioxidant composition of claim 1 wherein the secondary ingredients are present in the composition in an amount of 18% by weight.

4. The antioxidant composition of claim 1 wherein the bush plum pulp and skin is present in the composition in an amount of 2% by weight.

5. The antioxidant composition of claim 1 wherein the flavonoid is a flavonol and the flavonol is selected from the group consisting of quercetin, kaempferol, myricetin, analogues thereof, pharmaceutically acceptable salts thereof, and mixtures thereof.

6. The antioxidant composition of claim 5 wherein the flavonol is quercetin.

7. The antioxidant composition of claim 1 wherein the vitamin E forms are selected from the group consisting of alpha, beta, delta, and gamma tocopherol.

8. An antioxidant composition comprising quercetin, a mixture of alpha, beta, delta, and gamma tocopherols, grape skin extract comprising 30-82% polyphenols, green tea extract comprising 35-95% polyphenols, and bush plum pulp and skin comprising 5% vitamin C, wherein the quercetin and the mixture of tocopherols are present in the composition in an amount of from 30% to 85% by weight and in a weight ratio of from 40/60 to 90/10 percent and wherein the grape skin extract and the green tea extract are present in the composition in a weight ratio of from 60/40 to 80/20 percent and act in synergy to provide a higher antioxidant capacity.

9. The antioxidant composition of claim 8 wherein the weight ratios of the quercetin, the mixture of tocopherols, the grape skin extract, the green tea extract, and the bush plum pulp and skin are 49/33/9.5/6.5/2 percent, respectively.

10. The antioxidant composition of claim 8 wherein the composition has an antioxidant activity of at least 10,000 micromoles Trolox equivalent units per gram, using an ORAC(o) oxygen uptake measuring assay.

11. The antioxidant composition of claim 1 further comprising a carrier comprising gum acacia, xanthan gum, gum tragacanth, gum ghatti, and aloe vera gel extract; wherein the primary ingredients and the secondary ingredients are present in the composition in a weight ratio of 1:2, with respect to the carrier.

12. The antioxidant composition of claim 11 wherein the carrier comprises gum acacia, xanthan gum, gum tragacanth, gum ghatti, and aloe vera gel extract in a weight ratio of 30/30/20/19/1 percent, respectively.

13. The antioxidant composition of claim 11 wherein the composition is roller-compacted.

14. The antioxidant composition of claim 8 further comprising a carrier comprising gum acacia, xanthan gum, gum tragacanth, gum ghatti, and aloe vera gel extract; wherein the quercetin, the mixture of tocopherols, the grape skin extract, the green tea extract, and the bush plum are present in the composition in a weight ratio of 1:2 to 2:1, with respect to the carrier.

15. The antioxidant composition of claim 9 further comprising a carrier comprising gum acacia, xanthan gum, gum tragacanth, gum ghatti, and aloe vera gel extract in a weight ratio of 30/30/20/19/1 percent, respectively; wherein the quercetin, the mixture of tocopherols, the grape skin extract, the green tea extract, and the bush plum are present in the composition in a weight ratio of 1:2 to 2:1 with respect to the carrier and wherein the composition is roller-compacted.

16. An antioxidant composition comprising
quercetin,
a mixture of alpha, beta, delta, and gamma tocopherols,
grape skin extract comprising 30-82% polyphenols,
green tea extract comprising 35-95% polyphenols,
bush plum pulp and skin comprising 5% vitamin C, and
a carrier comprising gum acacia, xanthan gum, gum tragacanth, gum ghatti, and aloe vera gel extract;
wherein the quercetin and the mixture of tocopherols are primary ingredients and the primary ingredients are present in the composition in an amount of from 30% to 85% by weight in a weight ratio of from 40/60 to 90/10 percent;
wherein the bush plum pulp and skin, the green tea extract, and the grape skin extract are secondary ingredients and the secondary ingredients are present in the composition in an amount of from 15% to 70% by weight;
wherein the grape skin extract and the green tea extract are present in the composition in a weight ratio of from 60/40 to 80/20 percent; and
wherein the quercetin, the mixture of tocopherols, the grape skin extract, the green tea extract, and the bush plum pulp and skin are present in the composition in a weight ratio of 1:2 to 2:1, with respect to the carrier.

* * * * *